(12) United States Patent
Terada et al.

(10) Patent No.: US 8,134,131 B2
(45) Date of Patent: Mar. 13, 2012

(54) METHOD AND APPARATUS FOR OBSERVING INSIDE STRUCTURES, AND SPECIMEN HOLDER

(75) Inventors: Shohei Terada, Hitachi (JP); Kazutoshi Kaji, Hitachi (JP); Shigeto Isakozawa, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 197 days.

(21) Appl. No.: 12/329,661

(22) Filed: Dec. 8, 2008

(65) Prior Publication Data

US 2009/0302234 A1 Dec. 10, 2009

Related U.S. Application Data

(60) Continuation of application No. 11/755,894, filed on Jul. 11, 2007, now Pat. No. 7,476,872, which is a division of application No. 10/912,148, filed on Aug. 6, 2004, now Pat. No. 7,462,830.

(30) Foreign Application Priority Data

Sep. 18, 2003 (JP) .................................. 2003-325910

(51) Int. Cl.
*G21K 5/00* (2006.01)
(52) U.S. Cl. .................. 250/442.11; 250/306; 250/307; 250/310; 250/311; 250/440.11; 850/26; 850/28
(58) Field of Classification Search .................. 250/306, 250/307, 310, 311, 440.11, 442.11; 850/26, 850/28
See application file for complete search history.

(56) References Cited

U.S. PATENT DOCUMENTS

| | | | |
|---|---|---|---|
| 4,874,945 A | 10/1989 | Ohi | |
| 5,124,645 A * | 6/1992 | Rhoden et al. | 324/754.22 |
| 5,453,617 A | 9/1995 | Tsuneta et al. | |
| 5,475,218 A | 12/1995 | Kakibayashi et al. | |
| 6,242,737 B1 * | 6/2001 | Ohnishi et al. | 850/16 |
| 6,369,385 B1 * | 4/2002 | Muray et al. | 850/9 |
| 6,703,613 B2 | 3/2004 | Kaji et al. | |
| 6,734,687 B1 * | 5/2004 | Ishitani et al. | 324/750.19 |
| 6,750,451 B2 | 6/2004 | Koguchi et al. | |
| 6,841,775 B2 | 1/2005 | Kondo et al. | |

(Continued)

FOREIGN PATENT DOCUMENTS

JP 5-266849 A 10/1993

(Continued)

OTHER PUBLICATIONS

Takeo Kamino et al., "New Semiconductor Device Evaluation System for Sub-nanometer Area Failure Analyses", vol. 85, No. 4, 2003, pp. 305-310.

*Primary Examiner* — Michael Maskell
(74) *Attorney, Agent, or Firm* — Dickstein Shapiro LLP

(57) ABSTRACT

An object of the invention is to provide a method and apparatus for observing inside structures and a specimen holder, wherein aging degradation of a good sample to a bad sample can be tracked in the same field of view, using the same specimen in order to determine the mechanism of failure. The present invention is a method for observing inside structures. The method comprises irradiating a specimen with a corpuscular beam generated from a corpuscular beam source, detecting transmitted particles transmitted by the specimen, applying a voltage to a portion of the specimen, and observing of a detection status of the transmitted particles in the voltage-applied portion as needed.

3 Claims, 7 Drawing Sheets

U.S. PATENT DOCUMENTS

| | | |
|---|---|---|
| 6,858,851 B2 | 2/2005 | Tomimatsu et al. |
| 6,992,286 B2 | 1/2006 | Yaguchi et al. |
| 7,250,779 B2 * | 7/2007 | Dunklee et al. .......... 324/754.03 |
| 7,492,175 B2 * | 2/2009 | Smith et al. .............. 324/755.09 |
| 7,498,828 B2 * | 3/2009 | Dunklee et al. .......... 324/756.01 |
| 7,639,003 B2 * | 12/2009 | Dunklee et al. .......... 324/756.01 |
| 7,688,097 B2 * | 3/2010 | Hayden et al. ........... 324/755.03 |
| 7,761,983 B2 * | 7/2010 | Hayden et al. .................. 29/842 |
| 7,761,986 B2 * | 7/2010 | Gleason et al. ................ 29/876 |
| 2002/0027199 A1 * | 3/2002 | Inada et al. ................... 250/311 |
| 2004/0211899 A1 * | 10/2004 | Ezumi et al. .................. 250/310 |

FOREIGN PATENT DOCUMENTS

| | | |
|---|---|---|
| JP | 8-15318 A | 1/1996 |
| JP | 9-326425 | 12/1997 |
| JP | 2001-147070 | 5/2000 |
| JP | 2001-185593 A | 7/2001 |
| JP | 2002-83564 | 3/2002 |
| JP | 2002-157973 | 5/2002 |
| JP | 2003-35682 | 2/2003 |

* cited by examiner

METHOD AND APPARATUS FOR OBSERVING INSIDE STRUCTURES, AND SPECIMEN HOLDER

This application is a continuation of U.S. patent application Ser. No. 11/775,894, filed Jul. 11, 2007 now U.S. Pat. No. 7,476,872, which is a divisional of U.S. patent application Ser. No. 10/912,148, filed Aug. 6, 2004 now U.S. Pat. No. 7,462,830, claiming priority to Japanese Patent Application No. 2003-325910, filed Sep. 18, 2003, the entire disclosures of which are incorporated herein by reference.

BACKGROUND OF THE INVENTION

1. Field of the Invention

The present invention relates to a novel method and apparatus for observing the inside structure of a device while evaluating the performance of electronic devices, and to a specimen holder for the observation of inside structures.

2. Background Art

Conventionally, as a means of evaluating the electric characteristics of an electronic device, a prober is known wherein a probe is brought into contact with a semiconductor electronic device. For example, device characteristics are evaluated by bringing a probe into contact with an electrode for device evaluation while confirming the position using an optical microscope, thereby establishing electrical connection with an electrical measuring system. Also, the characteristics of a specific part of the device can be evaluated by bringing the probe into contact with an interconnection.

However, the observation of submicron interconnects is limited and it becomes difficult to bring the probe into contact with the finer interconnects with the confirmation of contact location of the probe using an optical microscope. To deal with this problem, Patent Document 1 discloses microscopic means which consists of an electron or ion irradiation system and a secondary electron detection unit for confirming a specific location within a sample with which the probe should be brought into contact, so that the probe contact position can be confirmed in a high resolution. Following the contact of the probe in a high resolution, a voltage contrast of secondary electrons detected by a scanning electron microscope can be obtained with 10 mV accuracy, enabling the observation of interconnection electric potential at a specific location during operation. Also, the use of a probe makes it possible to measure electrical characteristics, current-voltage characteristics, and the like only at a specific location.

In Patent Document 2, the use of a high-resolution compound microscope that has combined functions of a transmission electron microscope and a scanning probe microscope, such as an atomic force microscope, makes it possible to observe and measure inside structures, the surface structure of a plane parallel with the direction of incidence of an electron beam, mechanical characteristics, and electrical characteristics.

Patent Document 1: JP Patent Publication (Kokai) No. 9-326425 (1997)

Patent Document 2: JP Patent Publication (Kokai) No. 2002-279925

SUMMARY OF THE INVENTION

In Patent Document 1, although the electric potential of an interconnection on the surface of a specific location can be observed while the electronic device is in operation, the inside structure of the electronic device that is not exposed on the surface cannot be observed. Thus, in Patent Document 1, in order to observe the inside structure to find out the cause of aging degradation of electrical characteristics, following the measurement of the aging degradation of electrical characteristics, the degraded specimen is processed for a transmission electron microscope or a scanning transmission electron microscope, and then a comparison is made between the degraded specimen and a normal one. Therefore, at least two specimens must be prepared for observation, and it takes a long time for the analysis of the cause of aging degradation of electrical characteristics. Furthermore, as a specimen after degradation is observed, the elementary process such as the initial phase of degradation and the progress of degradation cannot be observed.

In Patent Document 2, while the surface of the plane parallel with the direction of incidence of an electron beam can be observed, it has been difficult to observe the inside structure of the specimen while voltage is being applied to a specific location.

An object of the present invention is to provide a method and apparatus for observing inside structures and a specimen holder for the observation of inside structures, whereby aging degradation of a good sample to a bad sample can be tracked in the same specimen and in the same field of view, so that the mechanism of failure can be observed.

The present invention enables observation of the inside structure of a specimen while applying a voltage to a specific location in the specimen. Specifically, the present invention is a method for observing inside structures, comprising irradiating a specimen with a corpuscular beam emitted from a corpuscular beam source, detecting transmitted particles transmitted through the specimen, applying a voltage to a portion of the specimen, and observing a detection status of the transmitted particles as needed in the voltage-applied location. Preferably, a voltage is applied to the specimen to cause a defect or an electrical characteristic change, and a detection status of the transmitted particles as needed as the specimen leads to the defect or the change of electrical characteristics due to voltage application is observed.

Also, the present invention is an apparatus for observing inside structures, comprising a corpuscular beam source, irradiation means for irradiating a specimen with a corpuscular beam from the corpuscular beam source, a detector for detecting transmitted particles transmitted through the specimen, and voltage application means for applying a voltage to a portion of the specimen.

Moreover, the present invention is a specimen holder for observing inside structures, comprising a specimen holder main body, a probe base disposed on the main body and provided with multiple probes, a specimen holding base positioned to face the probe base, the specimen holding base holding a specimen, and an interconnect connected to electrodes disposed on the probe base for applying a voltage to the electrodes.

According to the present invention, by observing the inside structure of an electronic device that is not exposed on the surface while measuring electrical characteristics of the electronic device, aging degradation of a good sample becoming a bad sample can be tracked in the same specimen and in the same field of view, and the mechanism of failure can be learned. Further, information on correlation between a change of electrical characteristics and a change of form and device distribution can be obtained by observing the inside structure while measuring electrical characteristics in the same filed of view in a microscopic region. Thus, a direct cause of the mechanism of failure can be obtained, which improves the efficiency of new product development and defect analysis measures.

According to the present invention, a method and an apparatus for observing inside structures and a specimen holder can be provided, wherein aging degradation of a good sample becoming a bad sample can be tracked and the mechanism of failure can be discovered in the same specimen and in the same field of view.

The following are preferred embodiments of the present invention. The present invention is not limited to the following embodiments.

DESCRIPTION OF THE PREFERRED EMBODIMENTS

Embodiment 1

Figure 1:
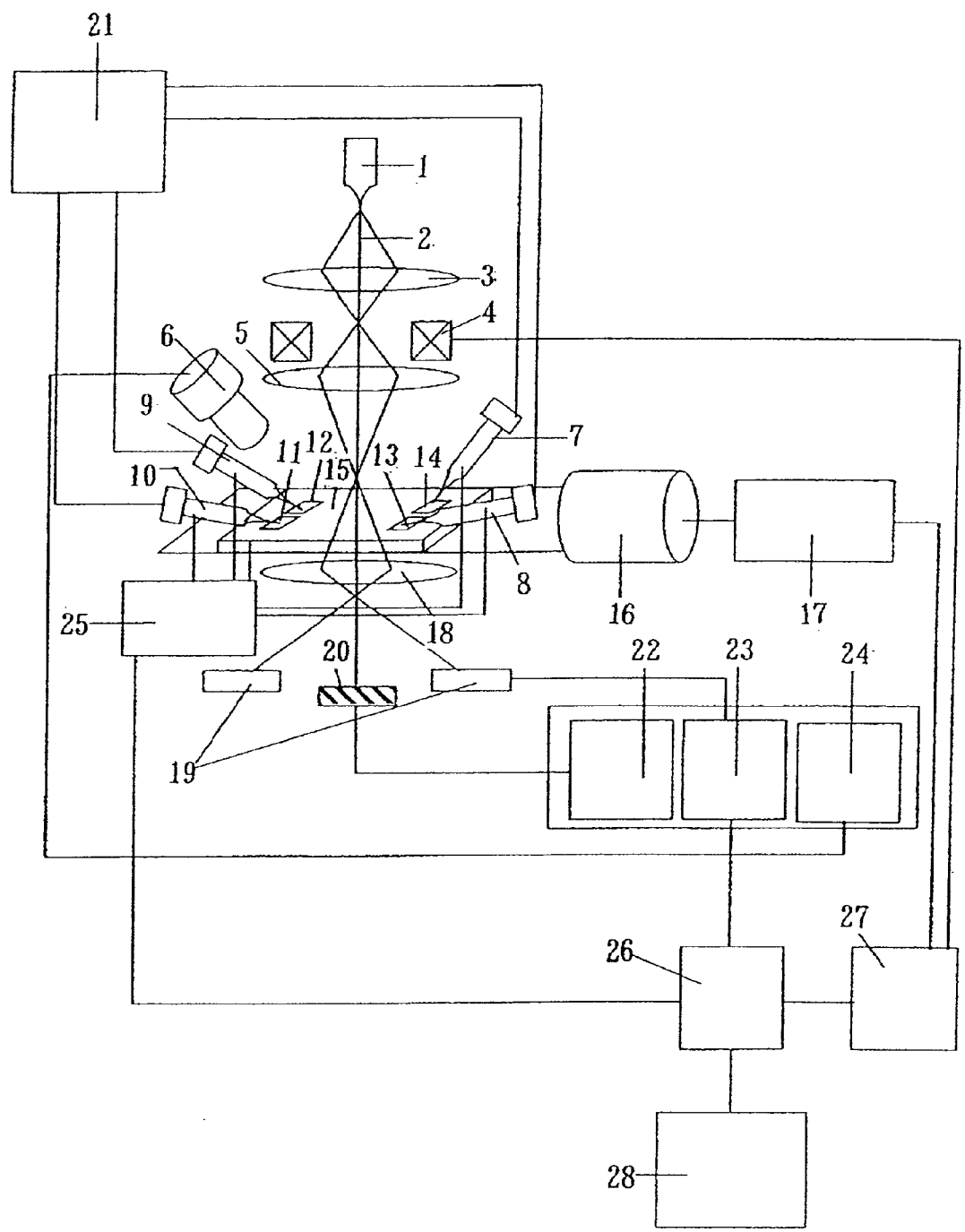
FIG. 1 shows the entire system of a scanning transmission electron microscope according to the present invention.

FIG. 1 shows the entire system of an apparatus according to the present invention that measures the electrical characteristics of a specimen and observes the inside structure of an electronic device using a scanning transmission electron microscope. The scanning transmission electron microscope comprises, in a high vacuum chamber, an electron emitter 1 that emits an electron beam 2 as a corpuscular beam, a condenser lens 3 that condenses the electron beam 2, a scanning coil 4 that scans the position of the electron beam with which an inserted specimen 15 is irradiated, and an objective lens 5. The electron beam 2 emitted from the electron emitter 1, after passing through the specimen 15, is magnified by a projector lens 18 in the middle. Transmitted electrons at the central part of the projector lens 18 are detected by a bright-field image detector 20, and displayed in a bright-field image monitor 22. Magnified transmitted electrons are detected by dark-field image detectors 19 and displayed in a dark field image monitor 23.

Electrical characteristics among electrodes 11, 12, 13, and 14 formed in the specimen 15 are measured by bringing probes 7, 8, 9, and 10 into contact with the electrodes 11, 12, 13, and 14, respectively, while confirming the position of the probes using a secondary electron detector 6 located within the scanning transmission electron microscope. The probes 7, 8, 9, and 10 are controlled by a probe transfer control unit 21 for coarse and fine adjustments as they are brought into contact with the electrodes 11, 12, 13, and 14. Voltage application to the probes 7, 8, 9, and 10 and measurement of electrical characteristics are made by a probe voltage control unit 25.

The specimen 15 is placed upon a specimen holder 16, and coarsely and finely moved by a specimen holder control unit 17. Either the probes 7, 8, 9, and 10 or the specimen 15 may be movable. The specimen 15 is moved in the present embodiment, wherein a piezoelectric device 41, which will be described later, is used for the fine adjustment, allowing control with nanometer precision.

Observation images captured into the dark-field image monitor 23 are detected by the dark-field image detectors 19, and all observation images are stored in a memory 28 after being sent to an image judgment unit 26 as needed. The image judgment unit 26 compares an image taken immediately after the beginning of observation with images captured during the observation and determines if there is any drift of the specimen position and the location where failure occurred in the observation location. If a drift of the specimen position is detected, a signal is sent to the scanning coil 4 or the specimen holder control unit 17 via a sample drift correction unit 27 in order to bring the specimen back to the original observation position.

As described above, in accordance with the correction mechanisms of the present embodiment for the drift correction of the probes 7, 8, 9, and 10 or the beam drift correction of the electron beam 2, an observation image prior to beam drift of the electron beam 2 by a change of electric potential of the probes 7, 8, 9, and 10 or the specimen 15 is stored in the memory 28. The mechanism includes a calculator that calculates the amount of drift by comparing an observation image after the drift with the stored image. The drift is then corrected by moving an irradiation area of the electron beam 2 only by the calculated drift amount, or by moving a specimen holding base 53 by the calculated drift amount with mechanical force. The correction mechanism may also calculate the drift amount of the specimen 15 in advance relative to the amount of voltage applied to the probes 7, 8, 9, and 10, and then add an amount of correction of the irradiation area of the electron beam 2 based upon the calculated drift amount.

Figure 2:
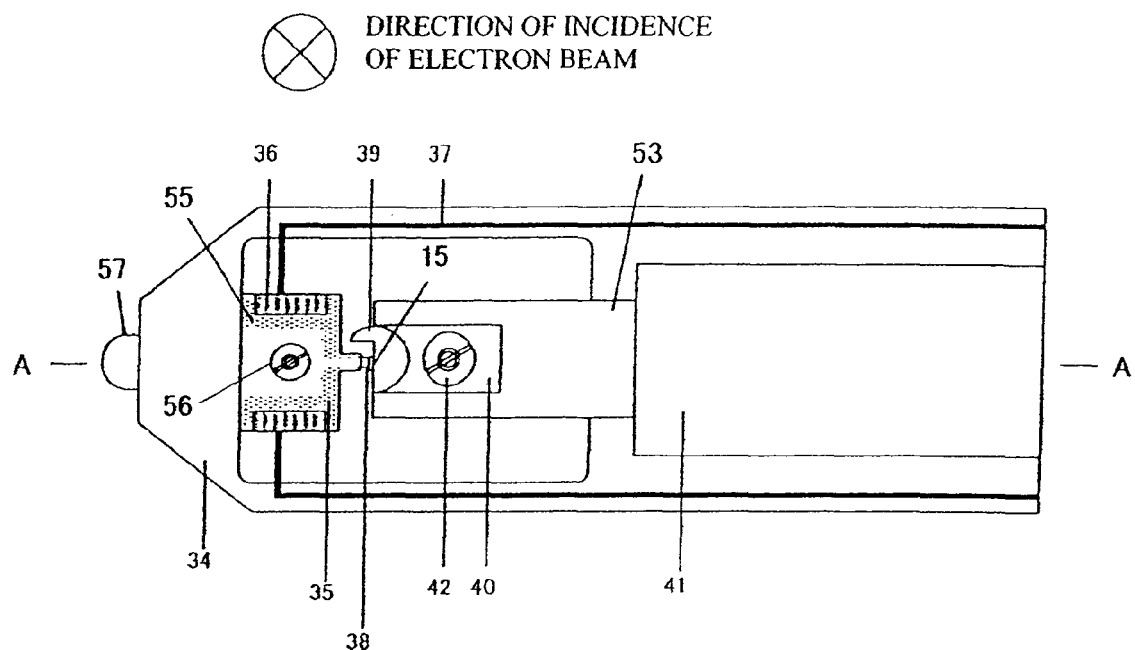
FIG. 2 is an overhead view of a specimen holder for transmission electron microscopes according to the present invention.
Figure 3:
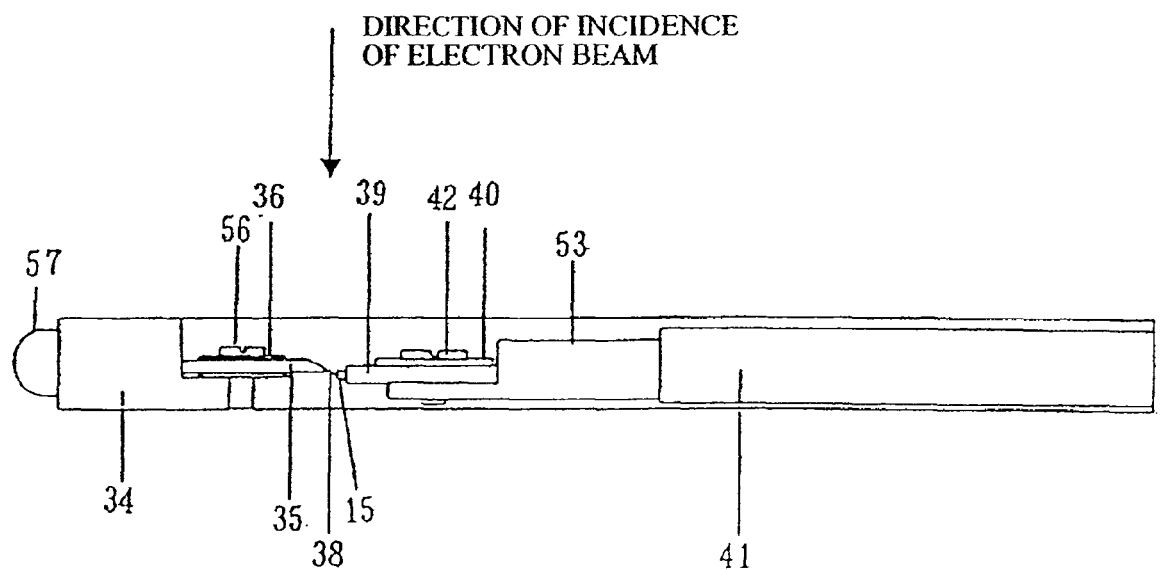
FIG. 3 is a cross section taken along A-A of the specimen holder of FIG. 2.

FIG. 2 is an overhead view of a specimen holder for transmission electron microscopes that is provided with a probe mechanism according to the present invention. FIG. 3 is a cross section taken along A-A of the specimen holder of FIG. 2. In the present embodiment, a side-entry specimen holder for scanning transmission electron microscopes that is provided with a probe mechanism unit is explained. The probe mechanism unit includes a probe base 35 and a probe 38 attached to it. The specimen holder for transmission electron microscopes is adapted to be inserted into a high vacuum chamber of a scanning transmission electron microscope from the side with the probe mechanism unit disposed on the holder.

At the tip of a main body 34 of the specimen holder for transmission electron microscopes, the probe base 35 provided with a gold interconnect 55 for electrodes shown in a mesh pattern can be disposed. The probe base 35 is pressed from above with a screw 56 through an electrode 36 for the probe base connected to four interconnects 37, thereby fixing the probe base 35 on the main body 34 of the transmission electron microscope specimen holder. Four probes 38 are disposed on the probe base 35, as shown in FIG. 1. A specimen mesh 39 is fixed on the specimen holding base 53 with a screw 42 after a specimen holding plate 40 is positioned. The specimen mesh 39 has a fine adjustment mechanism capable of moving in three axis directions perpendicular to one another using a piezoelectric device 41. Numeral 54 is a cavity and numeral 57 is a pivot.

Figure 4:
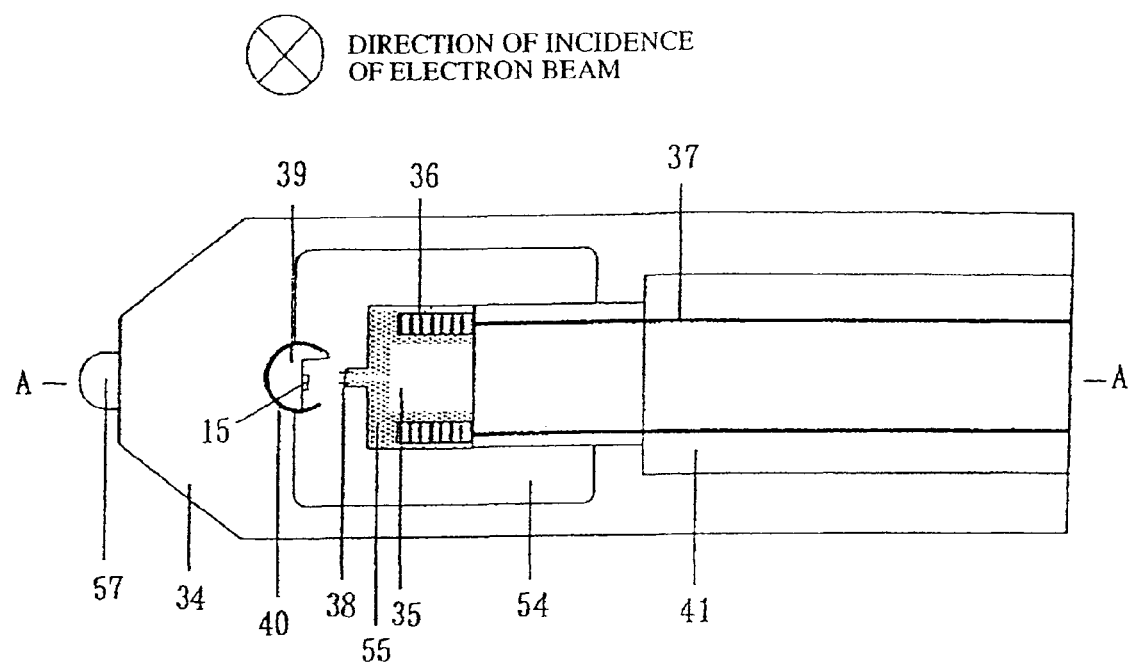
FIG. 4 is an overhead view of a specimen holder for transmission electron microscopes as another embodiment of the present invention.
Figure 5:
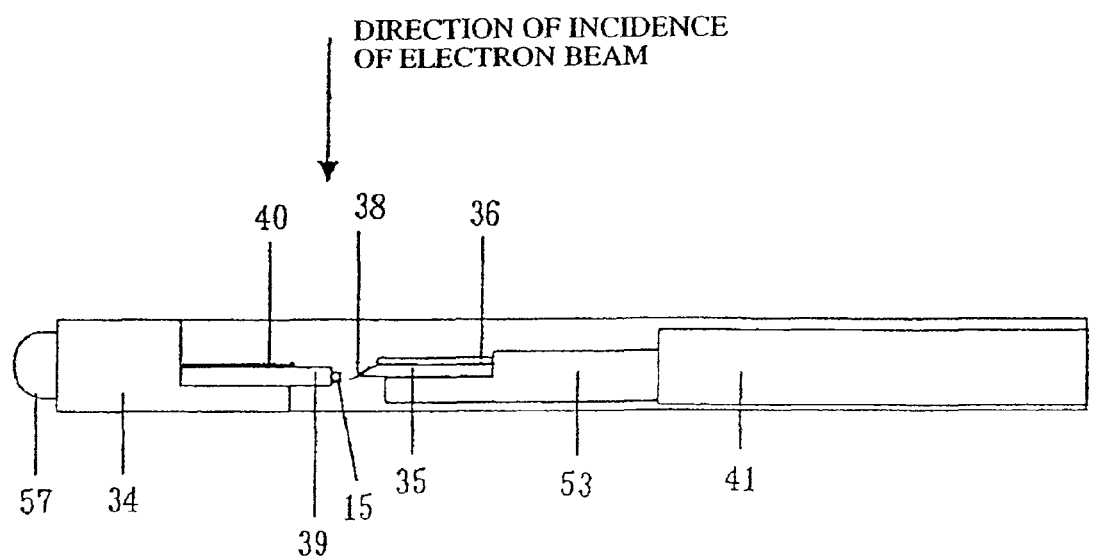
FIG. 5 is a cross section taken along A-A of the specimen holder of FIG. 4.

FIG. 4 is an overhead view of a specimen holder for transmission electron microscopes that is provided with a probe mechanism unit according to the present invention. FIG. 5 is a cross section taken along A-A of the specimen holder in FIG. 4. In the specimen holder for transmission electron microscopes shown in FIG. 4, the positions of the probe base 35 and the specimen mesh 39 are reversed from those in FIG. 2. In FIG. 4, a specimen is located toward the pivot 57. The probe base 35 can be moved in three axis directions perpendicular to one another by the piezoelectric device 41. In the specimen holder, two interconnects 37 connected to the electrodes 36 for the probe base can be housed within the specimen holder and do not become exposed, so that the specimen 15 and the probe base 35 can be exchanged easily.

Figure 6:
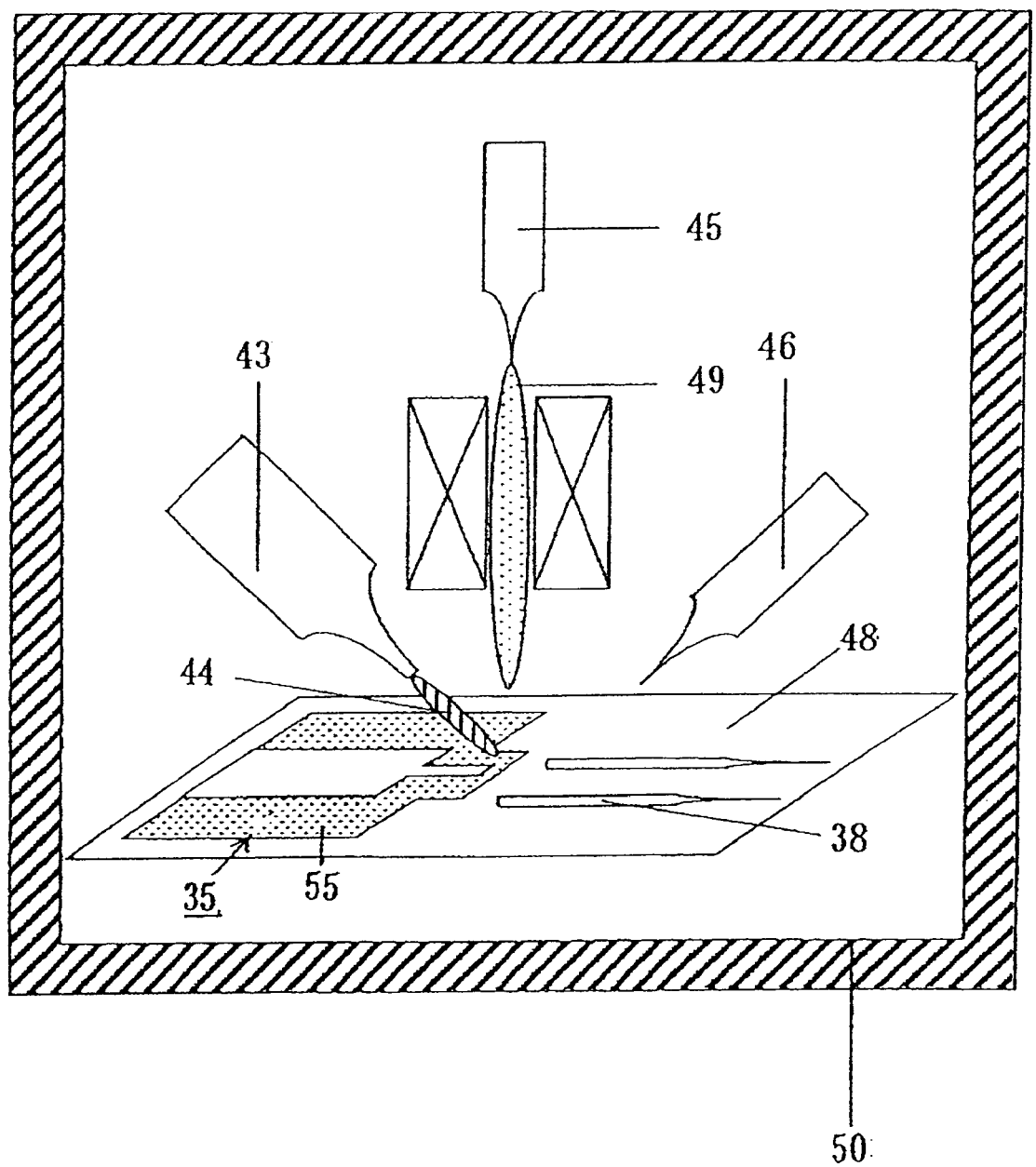
FIG. 6 is a cross section view of a focused ion beam unit for processing a probe mechanism unit.

FIG. 6 is a cross section view of an apparatus for producing the probe mechanism unit. A method of attaching two probes 38 to the probe base 35 is explained with reference to FIG. 6. Although the number of probes is four in FIG. 1, this is only an example. A focused ion beam unit 50 was used for attaching the probes 38 to the probe base 35.

First, on a specimen board 48 for a focused ion beam unit, the probe base 35 and the probes 38 are fixed with a carbon tape or double-sided tape, for example. Prior to insertion into the focused ion beam unit 51, the tip of the probes 38 was processed by electrolytic polishing to have a diameter of 1 μm or less.

Second, a manipulator 46 provided in the focused ion beam unit 50 is brought into contact with one of the probes 38. Then the probe 38 and the manipulator 46 are bonded to each other using tungsten supplied from a tungsten nozzle 44. After a rear portion of the probe 38 is cut to a specific length by a focused ion beam 49, it is moved upward. The manipulator 46 with the adhered probe 38 is moved near the center of the probe base 35, and then lowered until the probe 38 contacts the probe base 35. After the contact with the probe base 35 is confirmed, tungsten is supplied from the tungsten nozzle 44 and the probe 38 and the probe base 35 are bonded to each other. After the other probe is bonded in the same way, the probes 38 are disconnected by cutting the gold interconnect between them by the focused ion beam 49. Numeral 55 designates the gold interconnect.

In the present embodiment, the material of the probe 38 may include but is not limited to W, Pt—Ir alloy, and Pt. When using carbon nanotube or the like, with which it is difficult to produce a probe mechanism unit using the focused ion beam unit 50, the probe base 35 may be inserted into a carbon nanotube production unit for direct bonding.

Figure 7:
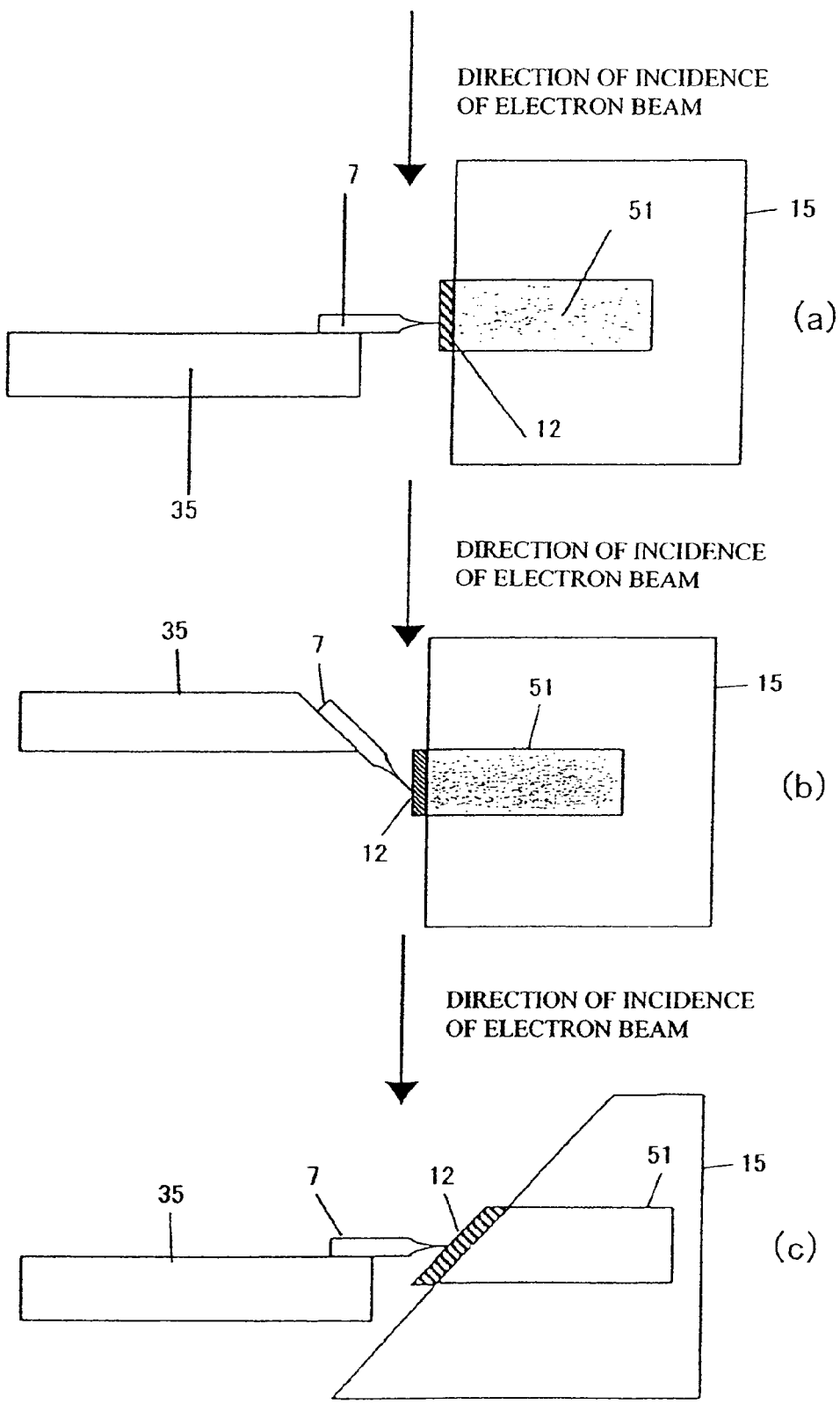
FIG. 7 is a cross section view that shows a positional relationship between a probe in the specimen holder and an electrode.

FIG. 7 is a cross section view that shows a positional relationship between a probe in the specimen holder and an electrode. In FIG. 7 (*a*), a probe 7 is adhered parallel to the probe base 35. In this case, the electrode plane of the electrode 12 disposed on the specimen 15 and the probe 7 are perpendicular to each other. In FIG. 7 (*b*), the tip of the probe base 35 is slanted at about 45 degrees and the probe 7 is adhered parallel to the slanted plane. In FIG. 7 (*c*), the electrode plane is inclined at about 45 degrees to the direction of incidence of an electron beam. In both FIGS. 7 (*b*) and (*c*), the angle between the electrode plane of the electrode 12 and the probe 7 is 90 degrees or less, so that they can be brought into contact with each other with a reduced contact resistance.

According to the present embodiment, the probe mechanism unit can be disposed in the specimen holder for scanning transmission electron microscopes, so that the specimen holder can be inserted into a scanning transmission electron microscope together with the probe mechanism unit in the same manner as a conventional specimen holder for scanning transmission electron microscopes. The interval between the probes of the probe mechanism unit can be set freely, so that the interval can be adjusted to the interval of the electrodes. Moreover, the angle of the probe can be set freely, so that a fine contact condition can be maintained between the probe and the electrode. The angle between the electrode plane of the electrode 12 and the probe 7 is not limited to the above example and may be determined such that the contact resistance can be minimized. Thus, the contact angle may be perpendicular or inclined.

Figure 8:
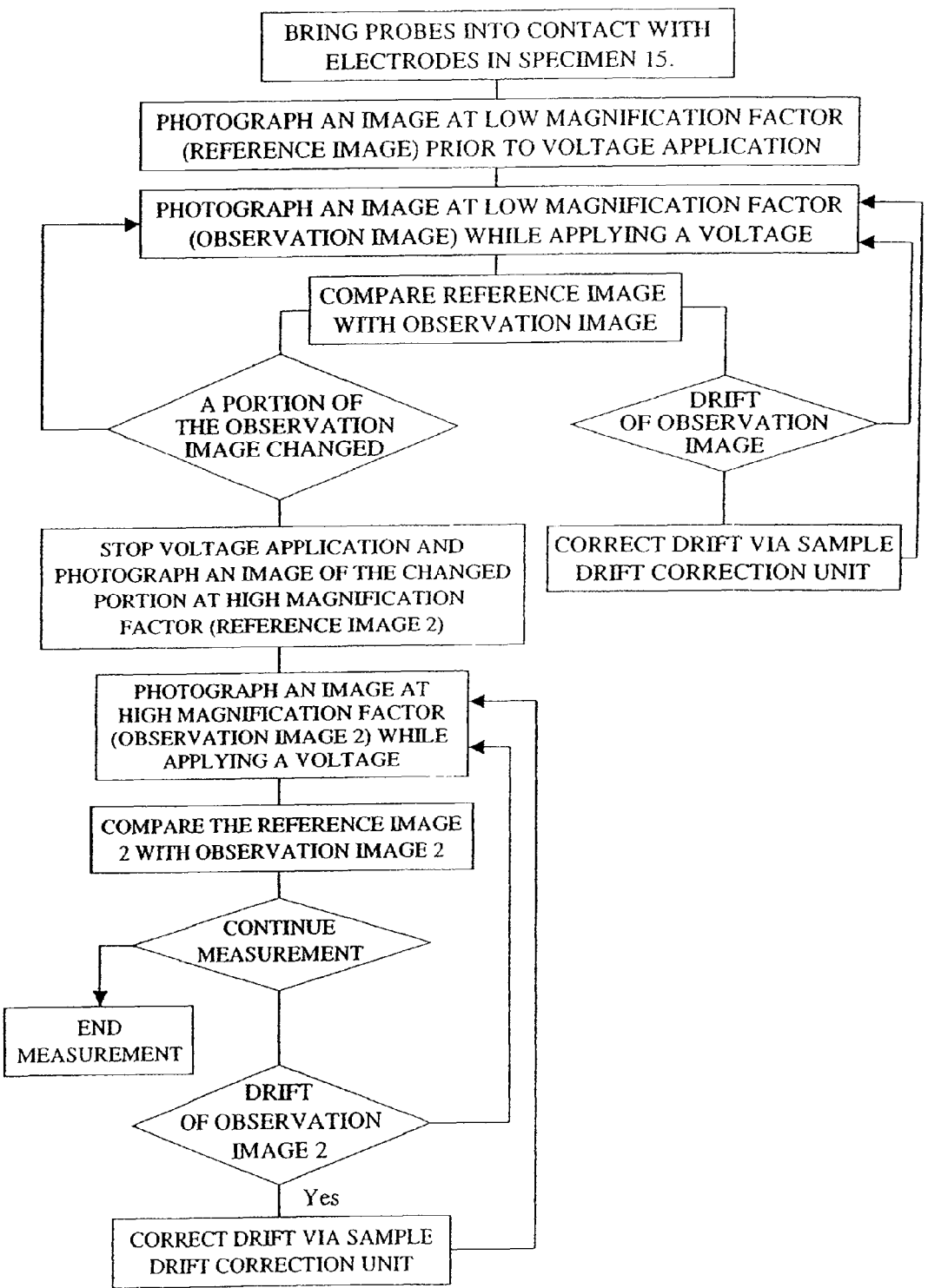
FIG. 8 is a block diagram of a method for observing the inside structure of a specimen while applying a voltage to the specimen using the apparatus of the present invention.

FIG. 8 is a block diagram of a method for observing the inside structure of a specimen while applying a voltage to the specimen using the apparatus of the present invention. Observation was made in the interconnects of an electronic device.

(1) The probes 7, 8, 9, and 10 are brought into contact with arbitrary electrodes 11, 12, 13, and 14, respectively, while confirming the location of each probe using the secondary electron detector 6. In the present embodiment, the location of the probes 7, 8, 9, and 10 is confirmed by the secondary electron detector 6, however, the confirmation method is not limited to this. For example, the location may be confirmed by detecting electric current flowing between the specimen and the probes.

(2) After the probes 7, 8, 9, and 10 are brought into contact with arbitrary electrodes 11, 12, 13, and 14, respectively, an image is taken prior to voltage application in a normal operating status with the magnification factor set to a low value (about 1000 to 5000×), and the image is stored as a reference image in the image judgment unit 26.

(3) To each of the probes 7, 8, 9, and 10 is applied a voltage. At the beginning of voltage application, the magnification factor is set to a low value and observation covers a wide area (observation image). The observation image is compared with the reference image in the image judgment unit 26.

(4) If a drift of the specimen (observation position drift) relative to the reference image is detected, a signal is sent from the sample drift correction unit 27 to the specimen holder control unit 17 or the scanning coil 4 to bring the observation position back to where it was at the beginning of observation. If no drift of the specimen is detected, observation is continued.

(5) If a change of a portion of the observation image is detected by comparing the reference image with the observation image, an image of the changed portion is taken at high magnification factor (about 100000 to 500000×), and the same voltage or an increasing voltage is applied until the specimen becomes a completely bad sample, while observing and photographing the inside structure as needed.

(6) Irradiation of the electron beam 2 is stopped and resistance is measured while a voltage is being applied. If the resistance value drops below a reference value, the specimen is regarded as a bad sample and an image of a portion of the interconnects is taken at high magnification factor (about 100000 to 500000×). The inside structure is then observed by detecting transmitted particles as needed while applying a voltage until the specimen becomes a completely bad sample. In this way, the structure of the specimen at every phase of the process of its becoming a completely bad sample can be learned, thus providing an indicator for new structures.

Specifically, a voltage is applied to the specimen to produce a defect or an electrical characteristic change, and a detection status of the transmitted particles as it leads to the defect or the electrical characteristic change due to voltage application is observed as needed. By "observe as needed" is herein meant taking an image of the same specimen at regular intervals, such as every second, every minute, or every hour, or taking consecutive images as a moving image for observation.

Also, in the present embodiment, the structure of a bad sample at every phase of its becoming a completely bad sample can be known, so that electronic devices can be inspected for bad samples in various stages of defectiveness relative to a good sample, and the location where failure occurred can be detected. Observed information includes migration of interconnects, void formation, and film breakage.

Moreover, according to the present embodiment, information about changes in electrical characteristics and the inside structure can be obtained by observing the inside structure while measuring electrical characteristics in the same filed of view in a microscopic region. Thus, a direct indicator of the mechanism of failure can be obtained, which improves the efficiency of new product development and defect analysis measures.

Embodiment 2

Figure 9:
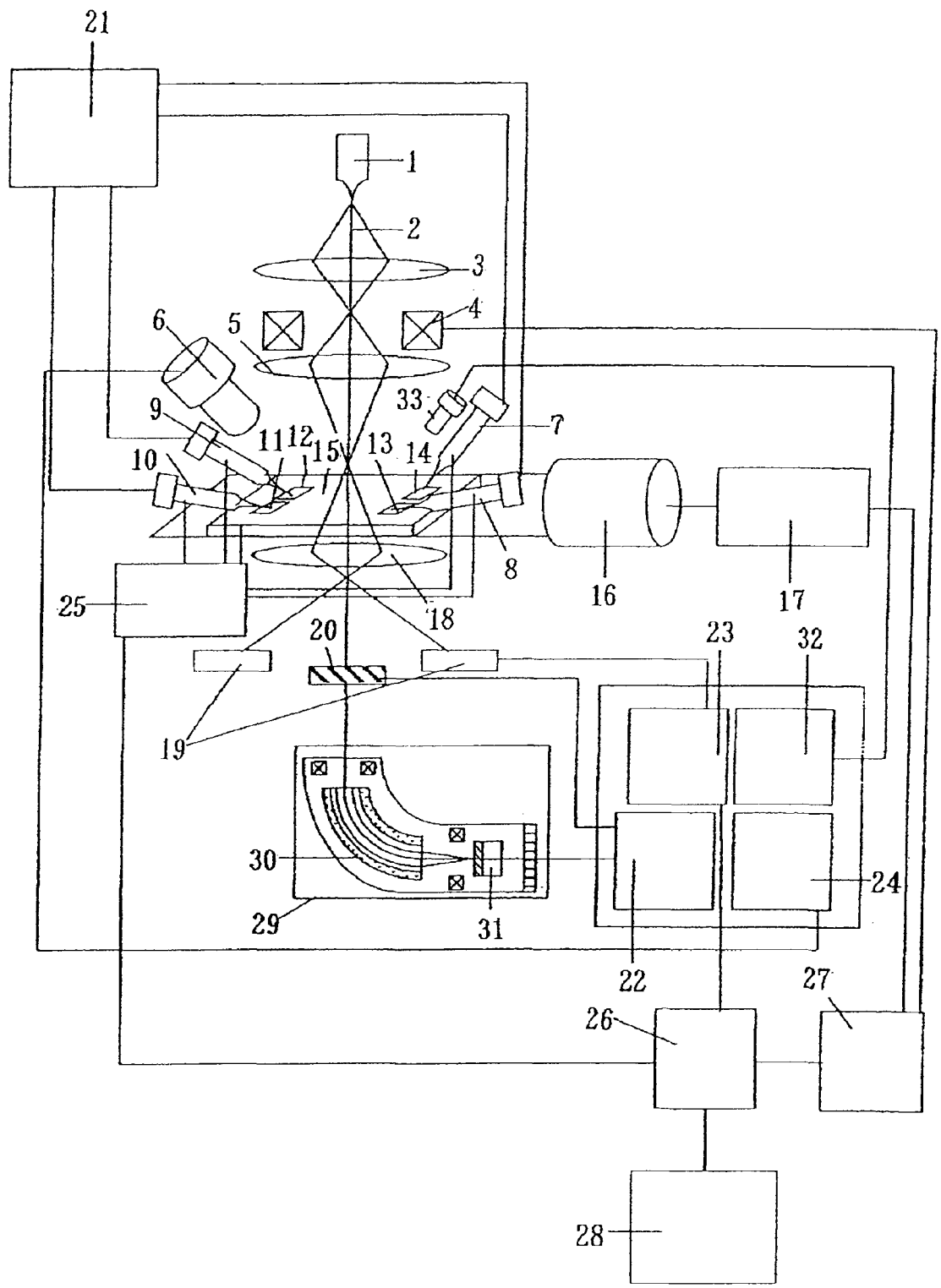
FIG. 9 shows the entire system of another scanning transmission electron microscope according to the present invention.

FIG. 9 shows the entire system of another example of the apparatus according to the present invention for measuring the electrical characteristics of a specimen and observing the inside structure of an electronic device using a scanning transmission electron microscope. The present embodiment differs from embodiment 1 in that an electron energy loss spectrometer (EELS) 29, an x-ray detector 33 that detects x-ray, and an x-ray monitor 32 are provided beneath the scanning transmission electron microscope. The electron energy loss spectrometer (EELS) 29 includes magnetic sector 30 and a detector 31 that detects a specific device selected by the magnetic sector 30. These units can capture an image of devices of interest and allow not only observation of an inside structure, but also observation of the internal movement of devices. Thus, information on devices can be obtained using these units, while taking structural images. In the present embodiment too, as in embodiment 1, by observing the inside structure as needed while applying a voltage until the specimen becomes a completely bad sample, information about change in every phase of the process of its becoming a completely bad sample can be learned, thereby providing an indicator for new structures.

Further, in the present embodiment, in a microscopic region, information on correlation between a change of electrical characteristics and a change of form and device distribution can be obtained while measuring electrical characteristics and observing the inside structure in the same filed of view. Thus, a direct indication of the mechanism of failure can be obtained, which improves the efficiency of new product development and defect analysis measures.

In the present invention, as in embodiment 1, a voltage is applied to the specimen to cause a defect or a change of electrical characteristics, and the detection status of transmitted particles as the specimen leads to a defect or the change of electrical characteristics due to voltage application is observed as needed.

In the present invention too, information can be obtained as to the structure of the specimen at every phase of the process of its becoming a completely bad sample. Thus, electronic devices can be inspected for bad samples in various phases relative to good samples.

While in the present embodiment, measurement of electrical characteristics and inside observation in a scanning transmission electron microscope have been described, this is only an example and any apparatus can be employed as long as it can observe the inside structure of a specimen.

What is claimed is:

1. A specimen holder which is adapted for lateral entry into an electron microscope, said specimen holder comprising:
   a specimen holder main body;
   a probe base disposed on said main body, disposed inside said specimen holder and provided with multiple probes;
   a specimen holding base positioned to face said probe base, said specimen holding base holding a specimen; and
   an interconnect connected to electrodes disposed on said probe base for applying a voltage to said electrodes; and
   wherein said specimen holding base has a specimen mesh which holds said specimen and has a fine adjustment mechanisim capable of moving in three-axis directions perpendicular to one another using a piezoelectric device.

2. The specimen holder for observing inside structures according to claim 1, wherein either said probe base or specimen holding base can be moved and includes a fine adjustment mechanism for three axis directions perpendicular to one another using a piezoelectric device.

3. The specimen holder for observing inside structures according to claim 1, wherein the contact angle between said probe and specimen is perpendicular or inclined.

* * * * *